US012806040B2

(12) United States Patent
Davidner et al.

(10) Patent No.: US 12,806,040 B2
(45) Date of Patent: Nov. 24, 2026

(54) FORCE SENSING DEVICES AND METHODS FOR ORTHOPEDIC SURGERY

(71) Applicant: OrthoIQ, LLC, Claremont, CA (US)

(72) Inventors: Alan Aaron Davidner, Claremont, CA (US); Anthony La Rosa, Rockaway, NJ (US); Philip Ormond Merritt, La Canada, CA (US); Michael Nogler, Oberperfuss/Tyrol (AT); José-Luis Moctezuma de la Barrera, Freiburg im Breisgau (DE); Colton Allen Ottley, Ivins, UT (US)

(73) Assignee: OrthoIQ, LLC, Claremont, CA (US)

( * ) Notice: Subject to any disclaimer, the term of this patent is extended or adjusted under 35 U.S.C. 154(b) by 0 days.

(21) Appl. No.: 19/249,057

(22) Filed: Jun. 25, 2025

(65) Prior Publication Data

US 2025/0387239 A1 Dec. 25, 2025

Related U.S. Application Data

(60) Provisional application No. 63/663,824, filed on Jun. 25, 2024.

(51) Int. Cl.

| | |
|---|---|
| ***A61F 2/46*** | (2006.01) |
| ***A61B 17/92*** | (2006.01) |
| ***A61B 34/30*** | (2016.01) |
| ***G16H 10/60*** | (2018.01) |

(Continued)

(52) U.S. Cl.

CPC ............ *A61F 2/4657* (2013.01); *A61B 17/92* (2013.01); *A61B 34/30* (2016.02); *G16H 10/60* (2018.01); *G16H 40/63* (2018.01); *A61B 2090/064* (2016.02); *A61F 2002/4666* (2013.01)

(58) Field of Classification Search

CPC ............................ A61F 2/4607; A61F 2/4657

See application file for complete search history.

(56) References Cited

U.S. PATENT DOCUMENTS

| | | | |
|---|---|---|---|
| 1,860,826 | A | 5/1932 | Tschudi |
| 3,127,941 | A | 4/1964 | Sieber |
| 4,909,419 | A | 3/1990 | Yamada et al. |

(Continued)

FOREIGN PATENT DOCUMENTS

| | | | |
|---|---|---|---|
| WO | 2022264145 | A1 | 12/2022 |
| WO | 2025106740 | A1 | 5/2025 |

OTHER PUBLICATIONS

International Search Report and Written Opinion re PCT/US2025/035159 mailed Sep. 3, 2025 (12 pages).

(Continued)

*Primary Examiner* — Andrew Yang

(74) *Attorney, Agent, or Firm* — Aurora Consulting LLC; Albert Du; Ashley Sloat

(57) ABSTRACT

An impaction device that may include a force transducer and optional accelerometer to measure an impact force between an impactor device and broach/implant or broach/implant handle. The impaction device may include a microcontroller electrically coupled to memory and the force transducer and optional accelerometer, wherein the microcontroller is configured to execute operations stored in the memory, the operations comprising: receiving resistive force data and acceleration data to calculate resistance for each impaction and generate a resistance curve for output to a display.

16 Claims, 8 Drawing Sheets

(51) Int. Cl.
*G16H 40/63* (2018.01)
*A61B 90/00* (2016.01)

(56) References Cited

U.S. PATENT DOCUMENTS

| | | | | |
|---|---|---|---|---|
| 5,025,869 | A | 6/1991 | Terunuma et al. | |
| 5,057,112 | A | 10/1991 | Sherman et al. | |
| 5,485,887 | A | 1/1996 | Mandanis | |
| 5,503,162 | A * | 4/1996 | Athanasiou | A61B 5/4514 702/158 |
| 6,959,478 | B2 | 11/2005 | Chen | |
| 7,588,093 | B2 | 9/2009 | Grand et al. | |
| 7,879,043 | B2 | 2/2011 | Meneghini et al. | |
| 7,963,430 | B2 | 6/2011 | Fukinuki et al. | |
| 8,236,005 | B2 | 8/2012 | Meneghini et al. | |
| 8,256,527 | B2 | 9/2012 | Wu | |
| 8,297,373 | B2 | 10/2012 | Elger et al. | |
| 8,348,120 | B2 | 1/2013 | Wei | |
| 8,485,276 | B2 | 7/2013 | Wei | |
| 8,678,262 | B2 | 3/2014 | Zhou et al. | |
| 8,696,756 | B2 | 4/2014 | Stein et al. | |
| 8,783,378 | B2 | 7/2014 | Zhou | |
| 8,978,951 | B2 | 3/2015 | Wei | |
| 8,979,758 | B2 | 3/2015 | Stein et al. | |
| 9,168,154 | B2 * | 10/2015 | Behzadi | A61B 34/10 |
| 9,271,675 | B2 | 3/2016 | Stein et al. | |
| 9,931,151 | B2 | 4/2018 | Donald et al. | |
| 10,071,009 | B2 | 9/2018 | Menke et al. | |
| 10,149,711 | B2 | 12/2018 | Bittenson | |
| 10,245,162 | B2 | 4/2019 | Behzadi et al. | |
| 10,406,664 | B2 | 9/2019 | Zhang et al. | |
| 11,490,943 | B2 | 11/2022 | Haiat et al. | |
| 11,696,770 | B2 | 7/2023 | Pedicini | |
| 11,766,381 | B2 | 9/2023 | Marton et al. | |
| 12,186,003 | B2 | 1/2025 | Wallace | |
| 2008/0125671 | A1 * | 5/2008 | Meneghini | A61F 2/4657 600/553 |
| 2009/0045241 | A1 | 2/2009 | Fukinuki et al. | |
| 2011/0094764 | A1 | 4/2011 | Wei | |
| 2011/0100662 | A1 | 5/2011 | Wei | |
| 2012/0232562 | A1 | 9/2012 | Mani et al. | |
| 2013/0204264 | A1 | 8/2013 | Mani et al. | |
| 2014/0135791 | A1 * | 5/2014 | Nikou | A61F 2/4609 606/130 |
| 2014/0262398 | A1 | 9/2014 | Gehret et al. | |
| 2017/0348010 | A1 * | 12/2017 | Chiang | A61B 90/03 |
| 2018/0055518 | A1 | 3/2018 | Pedicini | |
| 2018/0055553 | A1 | 3/2018 | Pedicini | |
| 2019/0216521 | A1 | 7/2019 | Chhatrala | |
| 2020/0294423 | A1 | 9/2020 | Blain et al. | |
| 2021/0321941 | A1 | 10/2021 | Behzadi | |
| 2022/0142693 | A1 | 5/2022 | Slocum et al. | |
| 2022/0151641 | A1 | 5/2022 | Lashure et al. | |
| 2022/0226033 | A1 | 7/2022 | Slocum et al. | |
| 2022/0233225 | A1 | 7/2022 | Pedicini et al. | |
| 2022/0240946 | A1 * | 8/2022 | Slocum | A61B 17/92 |
| 2022/0240998 | A1 | 8/2022 | Slocum | |
| 2022/0273317 | A1 | 9/2022 | Levy | |
| 2022/0323134 | A1 | 10/2022 | Lyon et al. | |
| 2022/0339769 | A1 | 10/2022 | Beer | |
| 2024/0024012 | A1 | 1/2024 | Dittrich et al. | |

OTHER PUBLICATIONS

International Search Report and Written Opinion mailed Feb. 14, 2025 re PCT/US2024/056010 (9 pages).

* cited by examiner

FIG. 7A
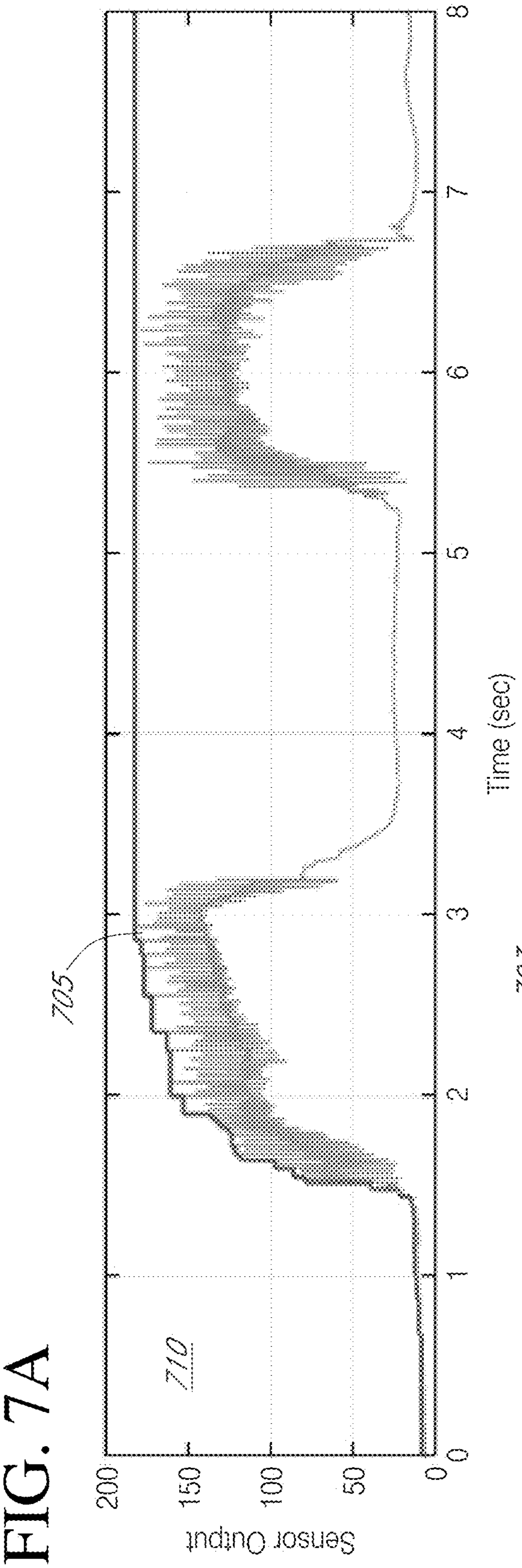
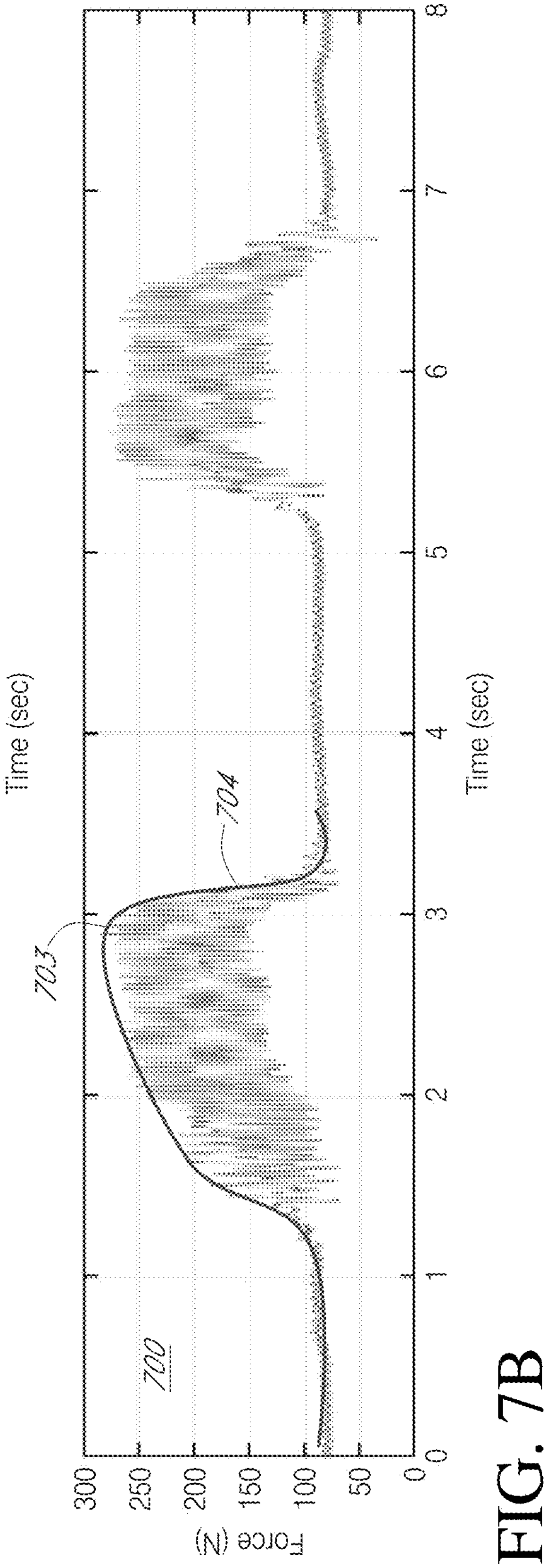
FIG. 7B

FORCE SENSING DEVICES AND METHODS FOR ORTHOPEDIC SURGERY

CROSS-REFERENCE TO RELATED APPLICATIONS

This application claims the priority benefit of U.S. Provisional Patent Application Ser. No. 63/663,824, filed Jun. 25, 2024, the contents of which are herein incorporated by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of orthopedic surgery (e.g., reconstructive surgery of the hip, knee, shoulder, and ankle), and, more specifically, to seating an implant or a broach in a bone during surgery. Described herein are systems and methods for easily, safely, and effectively seating an implant in a bone.

BACKGROUND

The frequency of Total Hip Arthroplasty (THA) procedures is expected to grow to 694,000 procedures by the year 2026. The procedure relieves pain and improves motion with little to no down time. THA is usually a safe and effective procedure with few complications. When complications do arise, they may require revision hip surgery. Revision hip surgery can cost upwards of $73,500, may result in long hospital stays, and serious co-morbidities are possible. Complications occur at a rate of about 3.5% and include instability and/or dislocation and, especially, peri-prosthetic femur fractures (i.e., fractures that occur around and, as a result of, the insertion of the broach, implant, or stem).

Additionally, the frequency of Total Shoulder Arthroplasty (TSA) procedures is expected to grow to 186,000 procedures by the year 2026. Like THA, TSA has equivalent complications. When complications arise, dislocation and periprosthetic fractures may also occur.

SUMMARY

In some aspects, the techniques described herein relate to an orthopedic automatic impaction system, including: a force transducer configured to measure a resistive force of at least one of: a broach, an implant, or a broach/implant handle; and a processor electrically coupled to memory and the force transducer, wherein the processor is configured to execute operations stored in the memory, the operations including: receiving resistive force data generated from the force transducer; generating a curve connecting a plurality of force data peaks of the generated resistive force data; and outputting the curve to a display.

In some aspects, the techniques described herein relate to an orthopedic manual impaction system including: an accelerometer configured to measure acceleration of a portion of a manual impaction device and at least one of: a broach, an implant, or a broach/implant handle; a force transducer configured to measure an impact force between the manual impaction device and at least one of: the broach, the implant, or the broach/implant handle; and a processor electrically coupled to memory, the force transducer, and the accelerometer, wherein the processor is configured to execute operations stored in the memory, the operations including: receiving resistive force data from the force transducer; receiving acceleration data generated from the accelerometer; calculating a resistance based on the resistive force data and the acceleration data; generating a resistance curve connecting the calculated resistance at each impaction of the manual impaction device; and outputting the curve to a display.

In some aspects, the techniques described herein relate to an orthopedic manual impaction system including: a first accelerometer configured to measure acceleration of a portion of a manual impaction device and at least one of: a broach, an implant, or a broach/implant handle; a second accelerometer configured to measure acceleration of a portion of a manual mallet; a force transducer configured to measure an impact force between the manual impaction device and at least one of: the broach, the implant, or the broach/implant handle; and a processor electrically coupled to memory, the force transducer, the first accelerometer, and the second accelerometer, wherein the processor is configured to execute operations stored in the memory, the operations including: receiving resistive force data from the force transducer indicative of net forces applied to the broach, the implant, or the broach/implant handle; receiving a first acceleration data generated from the first accelerometer indicative of acceleration of the broach, the implant, or the broach/implant handle; receiving a second acceleration data generated from the second accelerometer indicative of acceleration of the manual mallet; calculating a resistance based on the resistive force data, the first acceleration data, and the second acceleration data; generating a resistance curve based on the calculated resistance at each impaction of the manual impaction device; and outputting the curve to a display.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIGS. 7A-7B illustrate an embodiment of a first graphical representation (FIG. 7A) of impactions shown by data from the force transducer that is utilized to generate a second graphical representation (FIG. 7B) of resistive force data.

Figure 1:
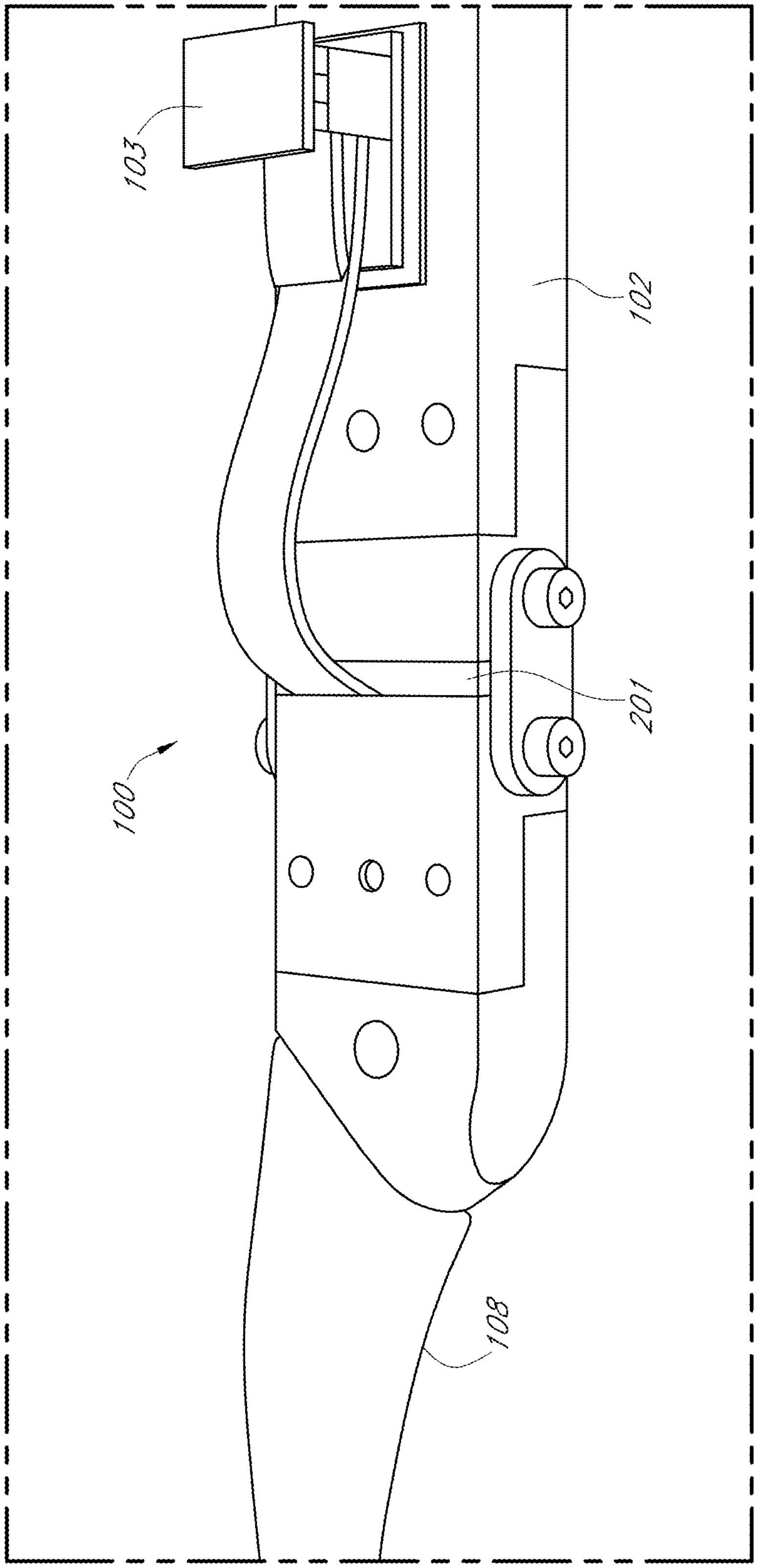
FIG. 1 illustrates a partial view of an embodiment of an impactor system with a broach/implant handle of an automatic impaction device coupled to a force transducer.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the claimed subject matter. Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Surgeons struggle with controlling the broaching and implant installation process, for example, during orthopedic surgeries (e.g., the femur, humerus, tibia, etc.). A small variance between swings of a manual mallet can create a large change in impact force between the swings, potentially resulting in bone fractures. Several factors may increase difficulty during the broaching process. For example, the large change in force of manual mallets resulting from little variance in swing or the large amplitude motors of impactors known in the art often do not include feedback options to control impact force. Further, for a manual mallet, a small change in velocity can result in a large change in force, where impaction force (F)=½ velocity squared/the distance of impact.

As a means of facilitating the broaching/implant process, broach/implant handles are utilized. Handles are implements that connect impactors to broaches and implants and function to transmit force. Broach/stem handles with strike plates also function to transmit force from a manual hammer. These broach/implant handles may be made of a large mass of stainless steel (e.g., approximately 2 pounds (lbs.)) to facilitate stiffness. A particular stiffness may function to transmit energy more effectively. Unfortunately, a large mass of stainless steel also absorbs some of the energy, therefore creating wasted energy. Wasted energy causes the surgeon to strike the broach handle with more force, further increasing stress on the implant and/or the bone. Finally, the surgeon works to overcome the perpendicular frictional force as the broach or implant is advanced into the bone canal. The frictional force is caused by the interaction of the broach or implant when compressing the cancellous bone.

The devices and methods described herein solve the above technical problems with technical solutions by providing a surgeon with a way to monitor the force applied to an implant or broach when manually or automatically impacting an implement such as an implant or broach.

As used herein, an implement may include, but not be limited to, a bone, a nail (pedicle), an impactor, a broach, a stem (implant), a handle, a mallet, etc. In some embodiments, the impactor may include impactors as described in U.S. patent application Ser. No. 18/948,017 which is herein incorporated by reference.

In order to determine optimal implant installation utilizing impactors, various sensors (e.g., force transducer(s), accelerometer(s), etc.) and their collected data may be evaluated. In some embodiments, resistive force may be monitored/collected by transmitting the force readings or signals (e.g., data) from a force transducer and/or acceleration readings or signals (e.g., data) from an accelerometer to a computing device or microprocessor. For example, the data may be analyzed utilizing the microprocessor, or the data may be transmitted, by wirelessly communicating, with a laptop, surgical robot, handheld device, display, virtual display, or computer, so that the installation of an implement can be memorialized. Alternatively, or additionally, the data may be stored locally in memory on the device or remotely on a server (i.e., having been wirelessly transmitted to the server).

In some embodiments, an optional display of the impactor system may present information to a user that may include a machine-readable mark (e.g., a Quick-Response (QR) code) on the manual mallet or impaction device. The machine-readable mark representing the data in the implement broaching/installation process can be downloaded by a machine-readable mark reader (e.g., handheld or bar code reader) and either printed and/or included in the patient's Electronic Medical Record (EMR). Therefore, the surgeon may have the opportunity to guarantee the implement installation. In an era of increasing demand for improved patient outcomes and reduced costs, this may provide a practical application of improving patient outcomes and implant longevity. The revision rate can be substantially reduced as a result of the impactor systems described herein. In the near future, when revision surgeries may be reimbursed less by third party payors, surgeries that result in revisions may not be economically viable. Already, surgeons that create too many femur or humerus fractures that result in revisions may lose their hospital or surgical center privileges.

FIG. 1 illustrates an embodiment of an impactor system for orthopedic implants with a broach/implant and broach/implant handle of an impaction device coupled to a force transducer. In some embodiments, the impactor system 100 includes a force transducer 201 between a broach/implant handle 102 and broach/implant 108. The force transducer 201 is electrically coupled to a microcontroller 103 (or processor(s)) and may be used to generate a force curve, optionally for display (e.g., as shown in FIGS. 2-5).

In some embodiments, the microcontroller 103 may include any suitable microcontrollers, integrated circuits, or processors with various architectures including any 16-bit or 32-bit microcontrollers (e.g., RX, AVR, PIC, MSP, etc.) utilizing complex (CISC) or reduced (RISC) instruction sets; any integrated circuit (e.g., application-specific integrated circuit (ASIC), field programmable gate arrays (FPGA), etc.); and/or any processor (e.g., x86/x64, ARM, etc.) capable of collecting force and acceleration data to generate a force curve and/or analyzing the data. In some embodiments, not shown, the force transducer 201 may be placed within the broach/implant handle 102 or, alternatively, between the broach/implant handle 102 and an anvil connector (not shown) of the broach/implant handle 102.

In some embodiments, the force transducer 201 may be a flexible device and/or other suitable microelectromechanical (MEM) device. Additionally, the force transducer 201 may include a Wheatstone bridge, a pressure transducer, mechanical force transducer, Linear Variable Differential Transformer (LVDT), or other suitable device that may collect force readings.

In some embodiments, the force transducer 201 may be tared (i.e., slightly preloaded) in order to more effectively establish a zero point and reduce noise of forces generated by different physiologies that may affect the resistive forces received from the force transducer. For example, the preload force can range from about 1 lb. (4.448 newtons (N)) to about 100 lbs. (444.8 N), about 5 lbs. (22.24 N) to about 80 lbs. (355.9 N), about 10 lbs. (44.48 N) to about 75 lbs. (333.6 N), about 20 lbs. (88.96 N) to about 70 lbs. (311.4 N), etc. In some embodiments, the force transducer 201 is tared with a force between about 1 lb. (4.448 N) and about 100 lbs. (444.8 N), about 1 lb. (4.448 N) and about 20 lbs. (88.96 N), about 20 lbs. (88.96 N) and about 80 lbs. (355.9 N), about 40 lbs. (177.9 N) and about 60 lbs. (266.9 N), etc.

In some embodiments, the force transducer 201 may be disposable, resposable, or reusable. For example, a force transducer 201 that is disposable may be sterilely stored until usage, used once, and then thrown away. In some embodiments, a force transducer 201 that is resposable may be used several times with resterilization after each use by sterilizing using an autoclavable or ethylene oxide (ETO) sterilization system more than one time, a plurality of times, hundreds of times, or thousands of times. In some embodiments, the force transducer 201 may be reusable with resterilization after each use.

In some embodiments, an automatic impaction device 107 may include a variable force trigger 121 on the handle 111. The variable force trigger 121 of the automatic impaction device 107 may be preset to a predefined force setting (i.e., a force applied to the broach/implant handle 102 over and over). By setting the variable force trigger 121 to a predefined force setting, an independent variable may be eliminated, thereby providing more accurate resistive force readings. In some embodiments, the variable force trigger 121 may be set to a predefined force setting through a selection of a trigger detent of a series of two or more trigger detents of the trigger of the automatic impaction device 107. Thus, the same impact force is applied at a rate of up to about 20 hertz (Hz) to about 23 Hz, about 15 Hz to about 30 Hz, about 10 Hz to about 35 Hz, etc. or more to an impactor/handle side of the force transducer 201. The rate of the impacts of the automatic impaction device 107 may generally be limited by the ability of the surgeon to hold the automatic impaction device 107 steady during impaction. The other side (e.g., the broach/implant side) of the force transducer 201 receives a force that is caused by increasing resistance from the broach/implant 108, for example, as the broach/implant is advanced into the intramedullary canal of a femur. In some embodiments, the force transducer 201 is capable of receiving resistive forces that can absorb between about 100 lbs. (444.8 N) to about 1000 lbs. (4448 N), about 200 lbs. (889.6 N) to about 800 lbs. (3558.6 N), about 400 lbs. (1779.3 N) to about 600 lbs. (2668.9 N) (e.g., about 500 lbs. or 2200 N of impact force), etc. In some embodiments, the force transducer 201 is capable of receiving a resistive force that is approximately more than double the actual impact force anticipated.

As shown, the broach/implant handle 102 may be connected to the broach/implant 108 for utilization in delivering the force impacts to the broach/implant 108. Upon implantation, the broach/implant 108 may be separated from the broach/implant handle 102. In some embodiments, the force transducer 201 is removed with the broach/implant handle 102. In some embodiments, the microcontroller 103 is electrically connected to the force transducer 201 through a cable, as shown in FIG. 1; however, any suitable electrical connection may be contemplated. For example, any direct connection of the force transducer 201 to the input/output pins of the microcontroller 103 may be considered. In some embodiments, the force transducer 201 may be integrated directly with the microcontroller 103.

Figure 2:
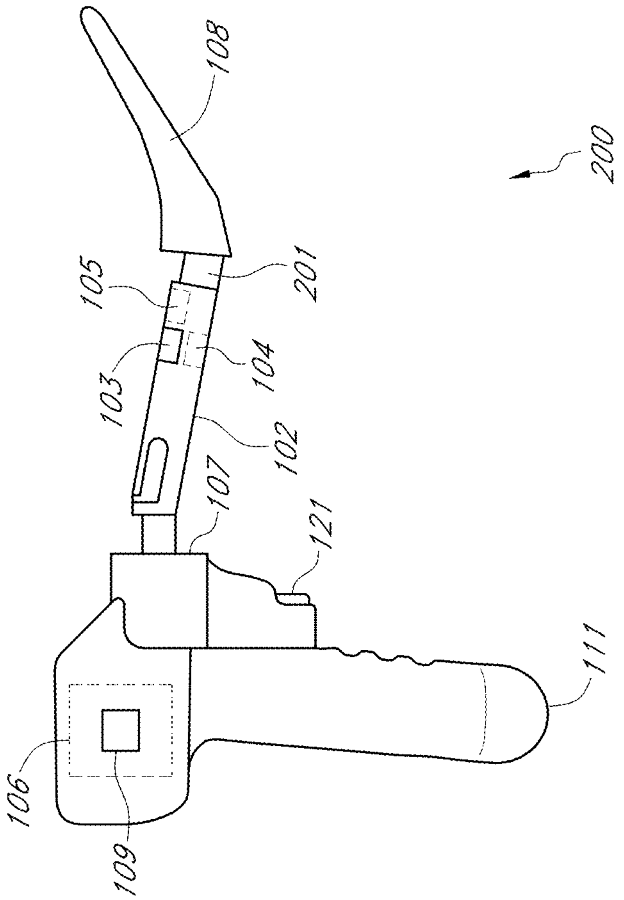
FIG. 2 illustrates an embodiment of an impactor system with a broach/implant and handle of a generic impaction device coupled to a force transducer.

FIG. 2 illustrates an embodiment of an impactor system 200 with a broach/implant handle 102 of an automatic impaction device 107 coupled to a force transducer 201. The force transducer 201 is electrically connected to a microcontroller 103, optional power source 104 (e.g., battery), and optional wireless module 105. In some embodiments, the optional power source 104 and/or optional wireless module 105 may be integrated into the microcontroller 103. In some embodiments, the optional wireless module 105 may utilize any suitable wireless communication protocol including wireless fidelity (Wi-Fi™), Bluetooth™, near field communications (NFC), etc. that may provide signals from the force transducer 201 and/or microcontroller 103 to an optional display 106 or output to a user device (not shown) in near real-time. In some embodiments, the optional power source 104 may be integrated into the microcontroller 103 and power both the microcontroller 103 and any connected device/modules such as the wireless module 105, optional display 106, and force transducer 201. In some embodiments, the power may be supplied to the microcontroller 103 and other device/s modules by a power source of the automatic impaction device 107.

In some embodiments, the automatic impaction device 107 includes an optional display 106. In some embodiments, the optional display 106 that may be placed on a portion of the automatic impaction device 107 that is not commonly utilized by the user during impaction (i.e., the user will not likely place their hands to put pressure on the display during the impaction). The optional display 106 may include easy viewing angles for near real-time resistive force display. For example, the display 106 may be on the back of the automatic impaction device 107 so that the user may view the graphical representation of the impaction data for an inflection point in the resistive force data when it occurs. The user, in some instances, may push on the back of the automatic impaction device 107; however, the user's hands may simply be on the handle 111 of the automatic impaction device 107 to direct the impacts generated by the automatic impaction device 107 into the target bone. In some embodiments, the optional display 106 may present generated resistive force diagrams to show users of the impactor system 200 near real-time resistive forces generated by each impaction. In some embodiments, the optional display 106 may show a machine-readable mark 109 or link to digital data showing the resistive force data (e.g., diagram). In some embodiments, as shown, the machine-readable mark 109 includes a QR (two dimensional bar) code that may be displayed on optional display 106 at the beginning, during, and/or end of the implant installation process, a one-dimensional barcode, a data matrix code, or other optical recognition mark or machine-readable zone that provides a presentation of the resistive forces during and/or after impaction of the broach/implant 108. In some embodiments, the optional display 106 may be communicatively coupled to the microcontroller 103 to present the generated resistive forces data directly on the optional display 106 in near real-time or present a machine-readable mark 109 or link to the generated resistive forces data. In this instance, because the impaction device is an automatic impaction device 107, the resistive forces data peaks are representative of the curve utilized to determine the inflection point (e.g., 603, 703, 705 of FIGS. 6, 7A, and 7B). The automatic impaction device 107 generates a constant force at a constant velocity and thus the generated resistive force data is representative of resistance (i.e., net force/net velocity). In some embodiments, the machine-readable mark 109 may be newly generated for each installation of a new broach/implant. In some embodiments, a machine-readable mark 109 may include data that shows historical implantations of past broaches/implants and may not change; however in such an instance, a display may not be needed, rather a machine-readable mark 109 representative of the data generated by each impaction device (e.g., automatic impaction device 107) may permanently be shown on each respective impaction device.

Figure 3:
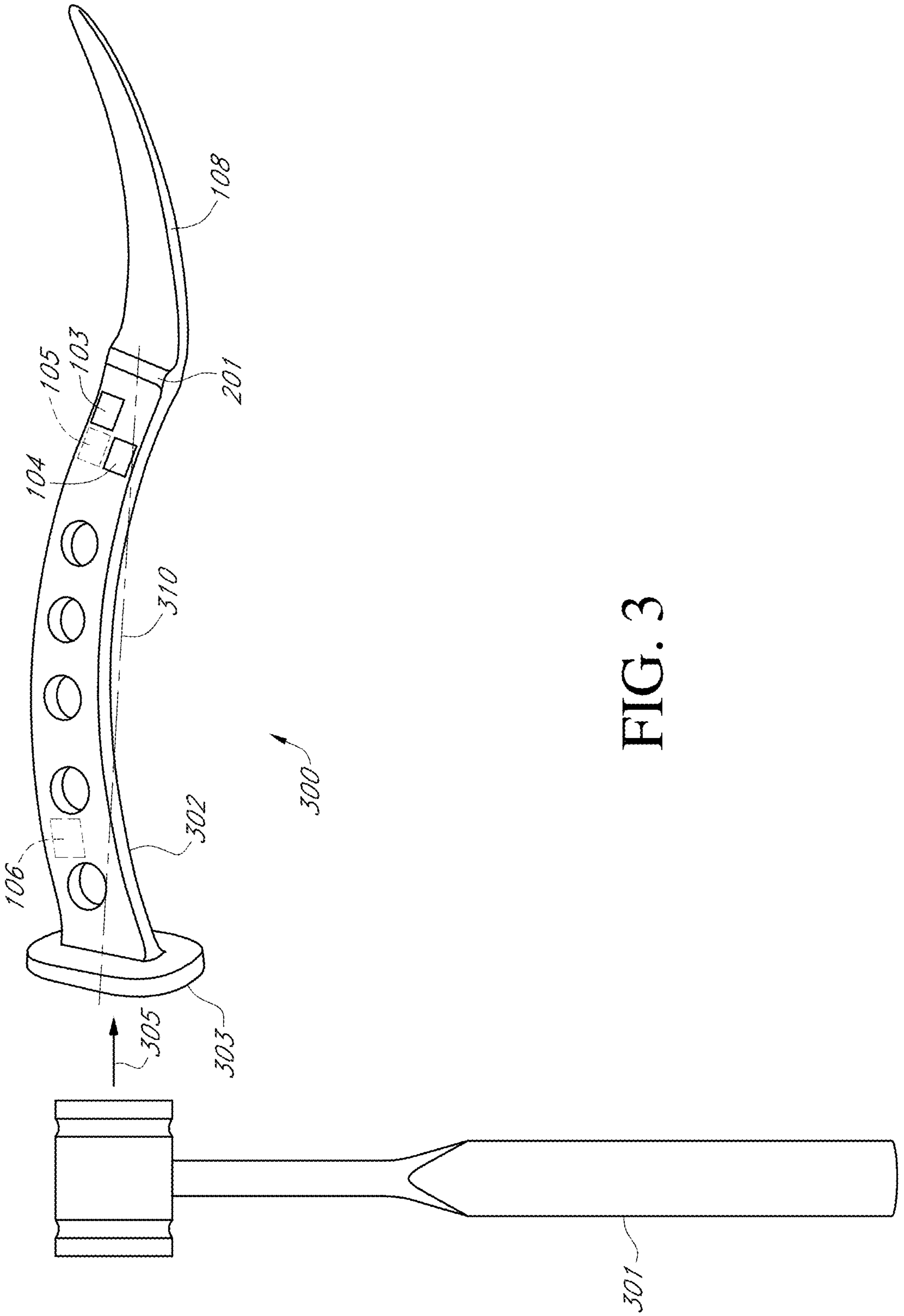
FIG. 3 illustrates an embodiment of an impactor system with a broach/implant handle coupled to a force transducer utilized with a manual mallet (not shown).

FIG. 3 illustrates an embodiment of an impactor system 300 with a broach/implant handle 302 coupled to a force transducer 201 utilized with a manual mallet 301. In some embodiments, the manual impactor system 300 may include a manual mallet 301, broach/implant handle 302, broach/implant 108, strike plate 303, and microcontroller 103 with optional display 106, power source 104, and optional wireless module 105. In such an impactor system 300, the manual mallet 301 may be utilized to hit, shown by arrows 305, the strike plate 303 to drive the broach/implant 108 into a patient's bone. In some embodiments, the user of the manual impactor system 300 may hold at least a portion of the broach/impactor handle 302 to direct the broach/implant 108 into the bone. In some embodiments, the optional display 106 is positioned on an under-utilized or un-utilized (i.e., unheld) portion of the broach/impactor handle 302. In some embodiments, not shown, the optional display 106 is adapted to the broach/implant handle 302 with a protruding mechanism that secures the optional display 106 to the broach/implant handle 302 while allowing the user to easily view resistive forces data on the optional display 106 during impaction. For example, the optional display 106 may extend orthogonal to a longitudinal axis 320 of the broach/implant handle 302 between the strike plate 303 and broach/implant 108 so that a user hitting the strike plate with the manual mallet (e.g., mallet 510 in FIG. 5) can view the display 106 from behind the broach/instrument handle 302. In some embodiments, the wireless module 105 (that may include Bluetooth™, Wi-Fi™ or other compatible wireless communications method) is connected to a microcontroller 103. In some embodiments, a machine-readable mark 109 is presented on the optional display 106 at the beginning, during, and/or end of the implement installation process.

Figure 4:
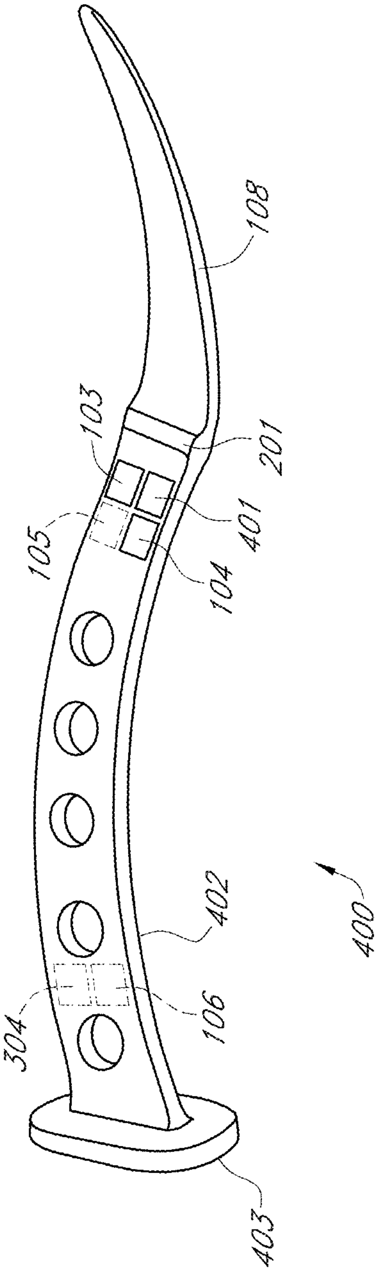
FIG. 4 illustrates an embodiment of an impactor system with a separate broach/implant handle with an accelerometer utilized with a manual mallet (not shown).

FIG. 4 illustrates an embodiment of an impactor system 400 with a separate broach/implant handle 402 with a force transducer 201 and an accelerometer 401. In some embodiments, the broach/implant handle 402 includes a strike plate 403 that is utilized when manual mallet (e.g., mallet 510 in FIG. 5) impacts the broach/implant handle 402 to drive the broach/implant 108 into a patient's bone. In some embodiments, a power source 104 and an optional wireless module 105 are connected to microcontroller 103.

In some embodiments, a force transducer 201 and accelerometer 401 may be used to calculate the resistance. The force transducer 201 (as positioned in FIGS. 1 and 2) may also be utilized to collect resistive force data that is utilized with the acceleration data to reduce noise and provide the user with resistance calculations. The resistance may be based on net applied forces based on the resistive force data and the acceleration (i.e., velocity) data of the broach/implant handle 402.

In some embodiments, a disposable, resposable (reusable for a number of times, but later disposable), or reusable accelerometer 401 is attached to a broach/implant handle 402. In some embodiments, the accelerometer 401 may include a piezoelectric, piezoresistive, or capacitive accelerometer. In some embodiments, the accelerometer 401 may also be a MEM device or part of an inertial measurement unit (IMU). The accelerometer 401 may have an about 200 g to about 600 g, about 100 g to about 1000 g, about 300 g to about 500 g, etc. acceleration range to prevent noise saturation. In some embodiments, the accelerometer 401 has an acceleration range of about 300 g to about 500 g. In some embodiments, a low pass filter is used to suppress the extraneous noise from the accelerometer 401. Noise saturation was found in testing with smaller acceleration range MEM accelerometers, for example, at about 60 g. Thus, higher sampling rates may also be used to improve the accuracy of the readings. For example, sampling rates of over about 5000 Hz may be utilized to improve accuracy of the acceleration readings.

Additionally, an optional wireless module 105 that is connected to or integrated with the microcontroller 103 may be utilized to wirelessly communicate resistive force data or machine-readable marks 109 to optional display 106 through receipt of such data by wireless receiver 304. In some embodiments, optional display 106 may be located on the broach/implant handle 402 similar to the locations described for broach/implant handle 302 above or may be remotely located.

Figure 5:
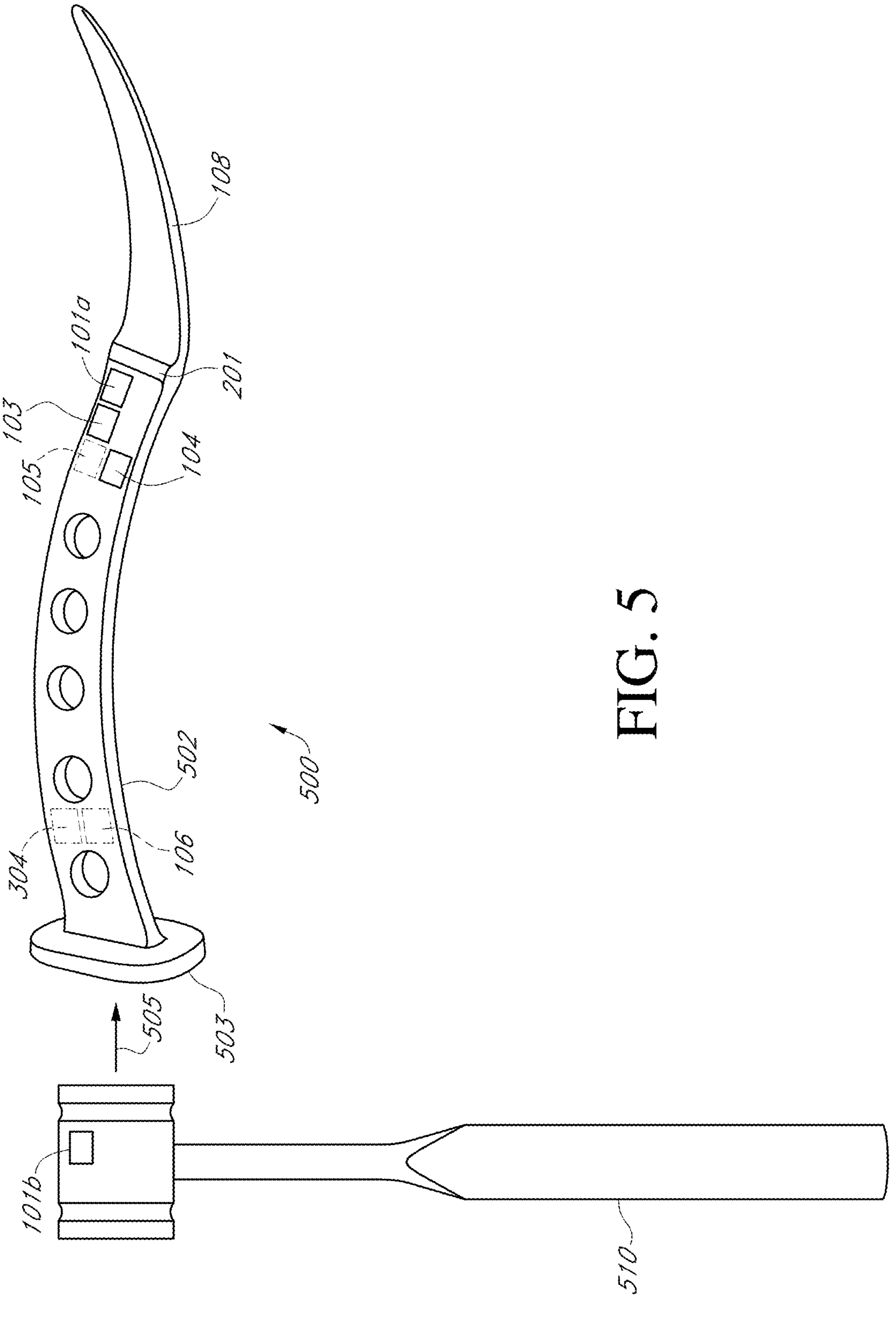
FIG. 5 illustrates an embodiment of an impactor system with a manual mallet with a first accelerometer and a separate broach/implant handle with a second accelerometer and force transducer.

FIG. 5 illustrates an embodiment of an impactor system 500 including a separate broach/implant handle 502 with a first accelerometer 101*a* and a force transducer 201 and a second accelerometer 101*b* in a manual mallet 510. The impactor system 500 includes abroach/implant handle 502 with a strike plate 503 that the manual mallet 510 may be utilized to hit, shown by arrows 505, to drive the broach/implant 108 into a patient's bone. In some embodiments, the first accelerometer 101*a* may provide acceleration data for the broach/implant handle 502 to show resistive acceleration of the broach/implant 108, and the second accelerometer 101*b* may provide acceleration data for the manual mallet 510 to better determine swinging force of a surgeon on the broach/implant 108 and for generating the resistance curve by calculating, at each impaction, a resistance with the net impaction force divided by net velocity (i.e., the net acceleration times time). The peak resistive forces may be utilized for the net impaction force, and the acceleration at the manual mallet 510 and acceleration at the broach/implant handle 502 may be utilized to calculate the net acceleration. The specifications of a surgeon's manual mallet 510 may be known and then provided to the microcontroller 103 to generate force data regarding each impact.

Figure 6:
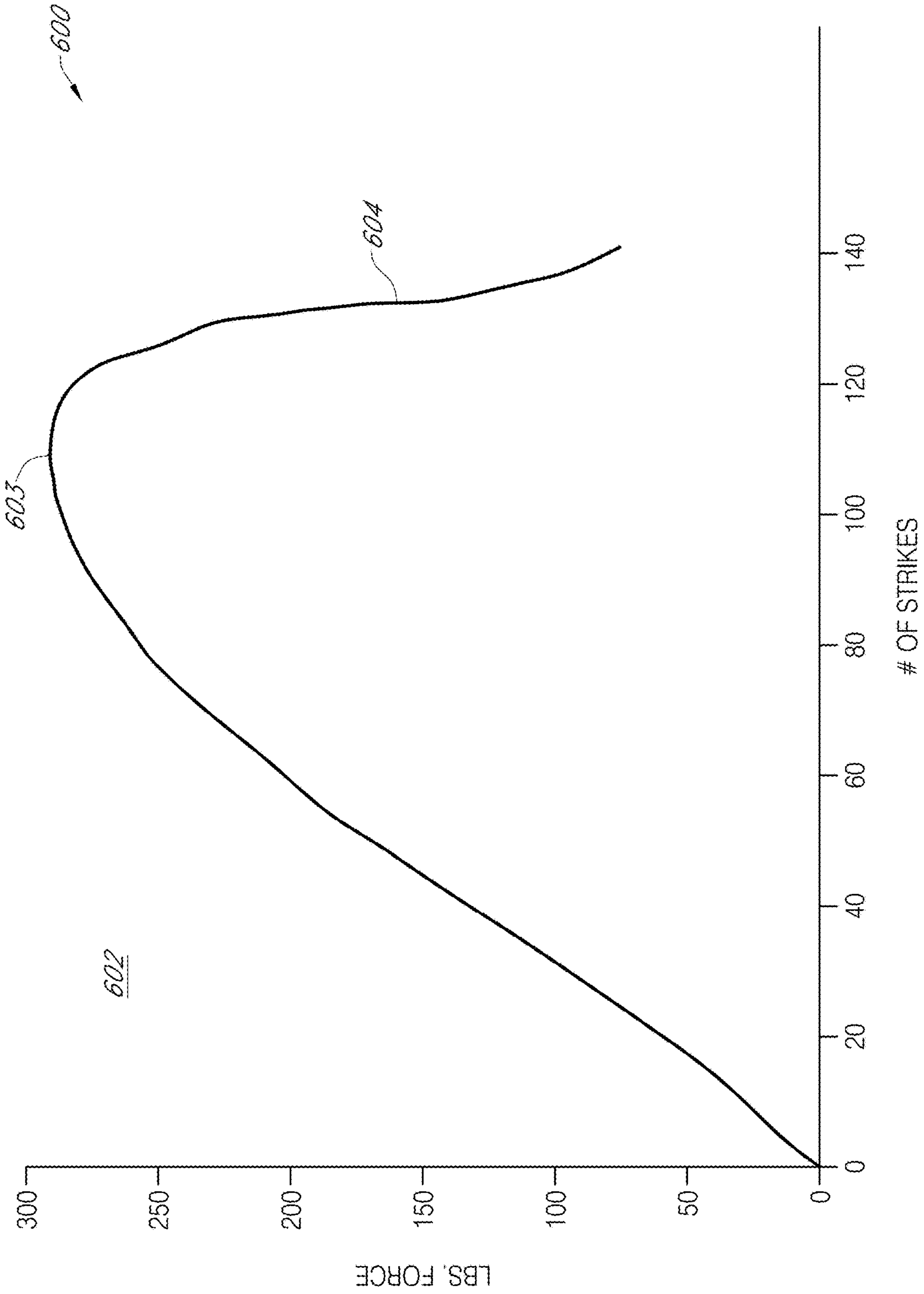
FIG. 6 illustrates an embodiment of a graphical representation of impactions shown by resistive force data measured by a force transducer of any of the above impactor systems.

FIG. 6 illustrates an embodiment of a graphical representation 600 of impactions shown by resistive force data measured by a force transducer 201 of any of the above impactor systems. FIG. 6 is a graphical representation 600 of the opposing resistive forces from an automatic impaction device (i.e., automatic impaction device 107 of FIG. 2) set at a predefined force. The graphical representation 600 shows the impact strikes and the opposing resistance of the broach/implant handle 102 as the broach is seated in a femur. Although other graphical representations are not shown, the graphical representation 600 may be replaced with any well-understood method of visualization including a bar graph or chart that may show resistive force over time. In some embodiments, the graphical representation 600 may include the number of strikes on the x-axis which generally represents time. When the broach/implant is fully seated with little to no further movement, the resistive forces (i.e., those shown in the y-axis) do not change significantly and the curve 602 that connects the peaks of the impact becomes relatively flat at, or surrounding, an inflection point 603. At the inflection point 603 of the curve where the curve begins to flatten out, the surgeon can then choose to shut off the automatic impaction device or alternatively reduce the force. However, a user (e.g., surgeon) may want to shut off/stop impaction before the inflection point 603. For example, as the user sees the curve's slope decrease over time, the user may elect to stop impaction. The curve is created by connecting the peaks of the impaction force spikes and then the resultant or combined impact force and resistive force that occur with each impact. In an exemplary embodiment of what a user does not want to see in curve 602, the graphical representation 600 includes a portion 604 that shows a steep or rapid decline in the resistive force that may result when impaction has included too many strikes and the femur cracks or gives way. In some embodiments, the force spikes are hidden from view and the surgeon may instead view a curve 602, for example on a display of a computing device or a display 106 of the automatic impaction device 107, as described elsewhere herein. Alternatively, the forces are displayed as columns, not shown, of a bar graph rather than as a fitted curve. In such an instance, the columns may include a resistive force indicator over the column as well. Furthermore, a manufacturer or a user, e.g., a surgeon, can establish the shut off point or a warning point, at the inflection point 603 or prior to the inflection point 603, for example, that can be incorporated into an algorithm that warns the surgeon or shuts off the automatic impaction device 107 automatically. In other words, the processor may execute instructions stored in memory, the instructions including receiving a plurality of sensor data (e.g., the acceleration data from the accelerometer and/or resistive force data from the force transducer), calculating resistance for each impaction, generating a data curve for resistive forces data or resistance over time (e.g., plotting each impaction), determining an inflection point in the data curve, and automatically shutting off the automatic impaction device when the data in the data curve approaches or reaches the inflection point (or a predetermined threshold and/or selection point). Alternatively, the processor may receive a plurality of historical data regarding the user (e.g., surgeon) and/or patient for the orthopedic procedure type, predict an inflection point from the historical data, and automatically shut off the automatic impaction device when the selection point and/or predetermined threshold of the data approaches or reaches the predicted inflection point. Still alternatively, the processor may receive a plurality of both the sensor data and the historical data, receive a selection point based on the historical data, and when the data of the data curve approaches or reaches the selection point, automatically shut off the automatic impaction device. The warning can be in many different forms: flashing visual indicators (e.g., yellow or red lights or some single or combination of colors); audible indicators or alarms; or force data with or without a curve representation. The data received from the force transducer 201 can be wirelessly communicated by a wireless module 105 of microcontroller 103 (as shown in FIG. 2) that is embedded in the broach/implant handle 102. The microcontroller 103 may wirelessly communicate to, for example, a surgical robot, computer, heads-up display, cell phone, a remote computing device, or any combination of mobile or immobile devices. The microcontroller 103 may include a microprocessor coupled to a memory. The memory being a non-transitory computer-readable storage medium. The microprocessor 103 may process operations stored in the memory and receive and process data from the force transducer 201 and/or optional accelerometer, as described elsewhere herein. The recorded data information can go into the patient record. The resistive force data can be encrypted to match hospital guidelines or protocols for wireless devices. Impaction force spike data may be used to determine a properly seated broach/implant and thus, may indicate when to cease impaction. For example, the difference between force spike peaks may be used to automatically cease impaction, generate a recommendation of ceasing impaction on a heads-up display or other computing device, or may be interpreted by a user to indicate the ceasing of impaction. An example case may be a predefined differential threshold, e.g., predefined by a user or a manufacturer, between a resistive force of an impact and a resistive force of a subsequent impact. When the differential between a resistive force of an impact and a resistive force of a subsequent impact is less than the predefined differential threshold (i.e., the slope of the resistive force curve is reducing (e.g., the curve is flattening)), the user may receive an indication to cease impaction, or an automatic stop to impaction by an automatic impaction device may occur. Further, impaction resistive force data may be graphed or otherwise output to a heads-up display or other computing device. Visual representation of impaction resistive force data (e.g., a graphical representation, a chart, or last impaction resistive force quantity display) may be used by a surgeon to determine proper deactivation of impaction on a broach/implant.

Additionally, in some embodiments, any of the impactor systems described herein may further include a camera or image sensor electronically connected to the processor/microcontroller. For example, the data, curve(s), and/or image(s) of the cortical rim from the image sensor of the impactor system attached to a broach handle, impactor, or equivalent can be digitally stored and/or placed in the patient history file. The data, curve(s) and/or cortical rim image(s) can be wirelessly communicated to a surgical robot, computer, or a myriad of mobile devices. These data and/or the data from the force transducer system can potentially reduce hospital/surgeon liability, maintain CMS (Centers for Medicare & Medicaid Services) reimbursement, and/or improve surgeon retention.

FIGS. 7A-7B illustrate an embodiment of a first graphical representation 710 (FIG. 7A) of two sets of impactions shown by data from a force transducer, e.g., force transducer 201 of FIG. 2, that is utilized to generate the second graphical representation 700 (FIG. 7B) of resistive force data. The graphical representations 700, 710 show data collected directly by the force transducer. The sensor data include an inflection point 705 of FIG. 7A very similar to the resistive force inflection point 703 of FIG. 7B. In some embodiments, the force transducer provides the force in newtons (N). Beyond the inflection point 703 of graphical representation 700, the impaction forces likely resulted in cracks in the bone of the implant (e.g., femur) as shown by the drop in resistive force 704.

Figure 8:
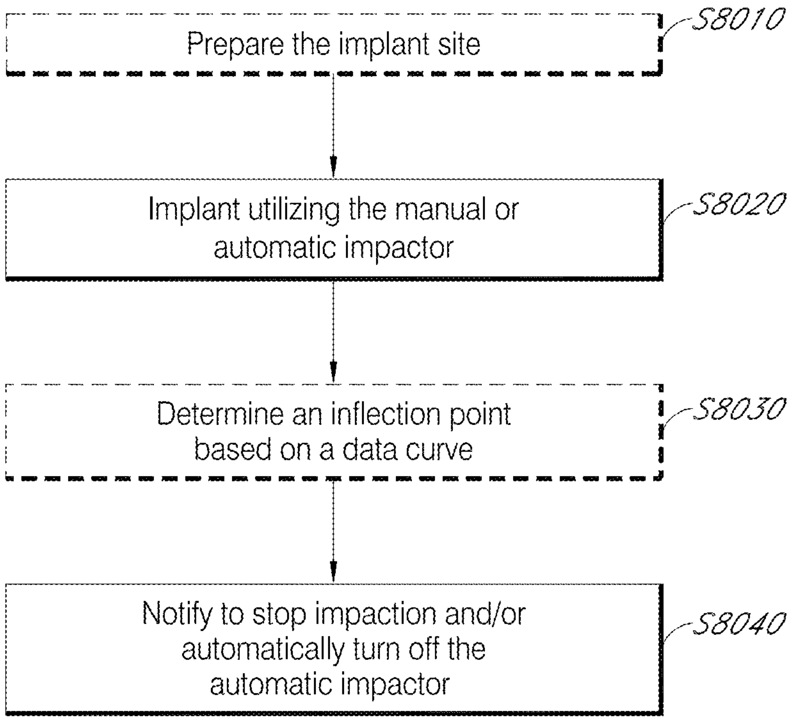
FIG. 8 illustrates an embodiment of an exemplary flow diagram showing the steps in operating an impactor system with a force transducer and/or accelerometer.

FIG. 8 illustrates an embodiment of an exemplary flow diagram showing the steps in operating an impactor system with a force transducer and/or accelerometer. In some embodiments, the flow chart includes steps to optionally prepare the implant site at block S8010; undergo the implantation process by utilizing a manual or automatic impaction device at block S8020; determine an inflection point based on a data curve (e.g., optionally present the resistive force curve or a resistance curve during the implantation for viewing by a user or automatically determine the inflection point using an algorithm) at block S8030; and optionally notify a user to stop impaction and/or automatically turn off the automatic impaction device at block S8040. The inflection point may be determined for a resistive force curve (when only a force transducer is utilized) or a resistance curve (when both a force transducer and one or more accelerometers are utilized). For automatic impaction devices, a resistive force curve is utilized because force and velocity are consistent (i.e., automated) based on presets by a user or a manufacturer. The algorithm may include a determination that the change in resistance and/or resistive force (i.e., the slope of the curve) is less than a predetermined threshold to provide a stopping point, for example before the inflection point. The predetermined threshold may be established by a user of the impaction device (or based on manufacturer specifications) or selected by the algorithm (e.g., utilizing an initial slope to determine a threshold slope that is a fifth, a quarter, a third, a half, etc. of the initial slope). For manual impaction devices, a resistance curve is utilized because force of each impaction is dependent upon the user's strength, angle of hitting the strike plate and other inconsistent variables. Thus, for the manual impaction device, a force transducer and one or more accelerometers may be used to calculate resistance rather than based on a resistive force. The notification, as described above, may include a warning that the force change may be slowing or an inflection point may be nearing or has occurred. Thus, a user may be notified to stop impaction, or an automatic impaction device may be automatically shut off. In some embodiments, the user may select the point (i.e., the selection point) that indicates where they believe (e.g., based on historical data, empirically determined, based on experience, etc.) the shut off point may be.

In some embodiments, the user may select this point in near real-time as they watch the resistive force curve slope reduce. In some embodiments, the selection point may be determined and selected by a user in advance of impaction. In some embodiments, the selection point is the predetermined threshold. In some embodiments, the selection point is based on a historical data utilizing a patient's physiological information (e.g., height, weight, musculature, age, sex, health issues, etc.), patient's past operations, similarity to other patients, etc. to predict a selection point for their body. In some embodiments, the selection point is well before the inflection point of the data curve in order to account for time to stop an automatic impaction device (e.g., automatic impactions may occur at a rate of about 20 Hz, by the time a user (i.e., surgeon) shuts off the impaction device, ten or more impactions may have occurred). In other words, in some embodiments, historical data with regard to each user's common impaction rate, reaction time, and historical number of impactions for a particular orthopedic surgery type may be utilized to better determine the selection point. For example, for a user that has a historical common impaction rate of 24 Hz and a reaction time of half a second, the selection point should account for at least 12 impactions before shut off (and potentially include a buffer). Thus, the selection point for this user may need to be at least 18 impactions before a predicted inflection point, or almost an entire second before. However, in some embodiments, the selection point may further be adjusted based on the patient's historical data. In such an example, for a patient that we predict to have an inflection point in about 40 impactions, the selection point may be at about the 20 impaction point. In some embodiments, for manual impactor devices, the selection point is stopped later, because a stopping point for a user may be immediate (i.e., without delay). In some embodiments, the predetermined threshold and selection point may be different and include different notifications/actions. In some embodiments, the selection point may notify the user that they should stop impaction, and the predetermined threshold may automatically shut off the automatic impactor. In other words, the selection point may provide a buffer time for a user to stop impactions, while the predetermined threshold may provide a safety net for the user to prevent damage to a patient.

EXAMPLES

Example 1. An orthopedic automatic impaction system, comprising: a force transducer configured to measure a resistive force of at least one of: a broach, an implant, or a broach/implant handle; and a processor electrically coupled to memory and the force transducer, wherein the processor is configured to execute operations stored in the memory, the operations comprising: receiving resistive force data generated from the force transducer; generating a curve connecting a plurality of force data peaks of the generated resistive force data; and outputting the curve to a display.

Example 2. The system of example 1, further comprising: receiving a selection point in advance or in near real-time, wherein the selection point indicates an impactor shut off point before, at, or after an inflection point in the curve.

Example 3. The system of any of the preceding examples, but particularly example 2, wherein the operations further comprise: triggering a notification to stop impaction when the impactor is approaching, or has met, the selection point.

Example 4. The system of any of the preceding examples, but particularly example 1, wherein the force transducer is one of: a flexible, a capacitive, a resistive, a Linear Variable Differential Transformer (LVDT), a microelectromechanical (MEM), a mechanical, or a piezoelectric force transducer.

Example 5. The system of any of the preceding examples, but particularly example 1, wherein the force transducer is disposable or reusable.

Example 6. The system of any of the preceding examples, but particularly example 1, wherein the operations further comprise taring the force transducer.

Example 7. The system of any of the preceding examples, but particularly example 6, wherein the force transducer is tared with about 1 pound (lb.) to about 100 lbs.

Example 8. The system of any of the preceding examples, but particularly example 1, wherein the operations further comprise: transmitting at least a portion of the resistive force data to an electronic medical record (EMR) of a patient.

Example 9. The system of any of the preceding examples, but particularly example 1, wherein the operations further comprise: transmitting the resistive force data from the force transducer to a computing device, wherein the computing device includes a mobile computing device, a surgical robot, or a virtual display.

Example 10. An orthopedic manual impaction system comprising: an accelerometer configured to measure acceleration of a portion of a manual impaction device and at least one of: a broach, an implant, or a broach/implant handle; a force transducer configured to measure an impact force between the manual impaction device and at least one of: the broach, the implant, or the broach/implant handle; and a processor electrically coupled to memory, the force transducer, and the accelerometer, wherein the processor is configured to execute operations stored in the memory, the operations comprising: receiving resistive force data from the force transducer; receiving acceleration data generated from the accelerometer; calculating a resistance based on the resistive force data and the acceleration data; generating a resistance curve connecting the calculated resistance at each impaction of the manual impaction device; and outputting the curve to a display.

Example 11. The system of example 10, wherein the operations further comprise: receiving a selection point in advance or in near real-time, wherein the selection point indicates an impactor shut off point before, at, or after an inflection point in the curve.

Example 12. The system of any of the preceding examples, but particularly example 11, wherein the operations further comprise: triggering a notification to stop impaction when the impactor is approaching, or has met, the selection point.

Example 13. The system of any of the preceding examples, but particularly example 10, wherein the operations further comprise: transmitting at least a portion of the resistance curve to an electronic medical record (EMR) of a patient.

Example 14. The system of any of the preceding examples, but particularly example 10, wherein the operations further comprise: transmitting at least a portion of the resistance curve to a computing device, wherein the computing device includes a mobile computing device, a surgical robot, or a virtual display.

Example 15. The system of any of the preceding examples, but particularly example 10, wherein the acceleration data is sampled at a rate of at least about 5000 hertz (Hz).

Example 16. An orthopedic manual impaction system comprising: a first accelerometer configured to measure acceleration of a portion of a manual impaction device and at least one of: a broach, an implant, or a broach/implant handle; a second accelerometer configured to measure acceleration of a portion of a manual mallet; a force transducer configured to measure an impact force between the manual impaction device and at least one of: the broach, the implant, or the broach/implant handle; and a processor electrically coupled to memory, the force transducer, the first accelerometer, and the second accelerometer, wherein the processor is configured to execute operations stored in the memory, the operations comprising: receiving resistive force data from the force transducer indicative of net forces applied to the broach, the implant, or the broach/implant handle; receiving a first acceleration data generated from the first accelerometer indicative of acceleration of the broach, the implant, or the broach/implant handle; receiving a second acceleration data generated from the second accelerometer indicative of acceleration of the manual mallet; calculating a resistance based on the resistive force data, the first acceleration data, and the second acceleration data; generating a resistance curve based on the calculated resistance at each impaction of the manual impaction device; and outputting the curve to a display.

Example 17. The system of example 16, the operations further comprise: receiving a selection point in advance or in near real-time, wherein the selection point indicates an impactor shut off point before, at, or after an inflection point in the curve.

Example 18. The system of any of the preceding examples, but particularly example 17, wherein the operations further comprise: triggering a notification to stop impaction when the impactor is approaching, or has met, the selection point.

Example 19. The system of any of the preceding examples, but particularly example 16, wherein the operations further comprise: transmitting at least a portion of the resistance curve to an electronic medical record (EMR) of a patient.

Example 20. The system of any of the preceding examples, but particularly example 16, wherein the operations further comprise: transmitting the resistance curve to a computing device, wherein the computing device includes a mobile computing device, a surgical robot, or a virtual display.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor on the point-of-care device and/or a local or remote processing subsystem. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

References in the specification to "one embodiment," "an embodiment" "an illustrative embodiment," "some embodiments," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. [0048] As used in the description and claims, the singular form "a", "an" and "the" include both singular and plural references unless the context clearly dictates otherwise. For example, the term "a force data peak" may include, and is contemplated to include, a plurality of force data peaks. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An orthopedic automatic impaction system, comprising:

an automatic impactor for orthopedic surgery;

a force transducer configured to measure a resistive force of at least one of: a broach, an implant, or a broach/implant handle during impaction by the automatic impactor; and a processor electrically coupled to memory and the force transducer, wherein the processor is configured to execute operations stored in the memory, the operations comprising:

receiving resistive force data generated from the force transducer;

generating a curve connecting a plurality of force data peaks of the generated resistive force data;

receiving a selection point of the curve based on a patient physiological information and historical data of a surgeon using the automatic impactor;

outputting the curve to a display; and triggering a notification to stop impaction or an automatic stop to impaction when the resistive force data is approaching, or has met the selection point.

2. The system of claim 1, further comprising: receiving the selection point in advance or in near real-time, wherein the selection point indicates an automatic impactor shut off point before, at, or after an inflection point in the curve.

3. The system of claim 2, wherein the notification includes a visual warning, audible warning, or a recommendation communicated to another computing device.

4. The system of claim 1, wherein the force transducer is one of: a flexible, a capacitive, a resistive, a Linear Variable Differential Transformer (LVDT), a mechanical, or a piezoelectric force transducer.

5. The system of claim 1, wherein the force transducer is disposable or reusable.

6. The system of claim 1, wherein the operations further comprise taring the force transducer.

7. The system of claim 6, wherein the force transducer is tared with about 1 pound (lb.) to about 100 lbs.

8. The system of claim 1, wherein the operations further comprise: transmitting at least a portion of the resistive force data to an electronic medical record (EMR) of a patient.

9. The system of claim 1, wherein the operations further comprise: transmitting the resistive force data from the force transducer to a computing device, wherein the computing device includes a mobile computing device, a surgical robot, or a virtual display.

10. An orthopedic impaction system, comprising:

an automatic impactor for orthopedic surgery;

a force transducer configured to measure a resistive force of at least one of: a broach, an implant, or a broach/implant handle during impaction by the automatic impactor; and a processor electrically coupled to memory and the force transducer, wherein the processor is configured to execute operations stored in the memory, the operations comprising:

receiving resistive force data generated from the force transducer;

generating a curve connecting a plurality of force data peaks of the generated resistive force data; and triggering a notification to stop impaction or an automatic stop to impaction when the automatic impactor is approaching, or has met, a selected point of the curve based on a patient physiological information and historical data of a surgeon using the automatic impactor, wherein the historical data includes one or more of: a common impaction rate, a reaction time, and a historical number of impactions for the surgeon for a particular orthopedic surgery type.

11. The system of claim 10, wherein the operations further comprise:

receiving the selected point of the curve in advance or in near real-time, wherein the selected point indicates an automatic impactor shut off point before, at, or after an inflection point in the curve.

12. The system of claim 11, wherein the notification includes a visual warning, audible warning, or a recommendation communicated to another computing device.

13. An orthopedic impaction system, comprising:

an automatic impactor applying a predetermined impaction force at a predetermined rate of impaction;

a force transducer configured to measure a resistive force of at least one of: a broach, an implant, or a broach/implant handle during the impaction by the automatic impactor; and a processor electrically coupled to memory and the force transducer, wherein the processor is configured to execute operations stored in the memory, the operations comprising:

receiving resistive force data generated from the force transducer;

generating a curve connecting a plurality of force data peaks of the generated resistive force data; and triggering a notification to stop impaction or an automatic stop to impaction when the automatic impactor is approaching, or has met, a selected point of the curve based on a patient physiological information and historical data of a surgeon using the automatic impactor, wherein the historical data includes one or more of: a common impaction rate, a reaction time, and a historical number of impactions for the surgeon for a particular orthopedic surgery type.

14. The system of claim 13, further comprising: receiving the selected point in advance or in near real-time, wherein the selected point indicates an automatic impactor shut off point before, at, or after an inflection point in the curve.

15. The system of claim 13, wherein the selected point is further based on historical data of the patient and includes past operations of the patient and/or similarity to other patients.

16. The system of claim 13, wherein the predetermined rate of impaction is up to about 35 hertz.

* * * * *